United States Patent
Ko

(10) Patent No.: US 9,482,624 B2
(45) Date of Patent: Nov. 1, 2016

(54) APPARATUS FOR INSPECTING

(71) Applicant: Sunmoon University Industry-University Cooperation, Asan-si (KR)

(72) Inventor: Kuk Won Ko, Seongnam-si (KR)

(73) Assignee: Sunmoon University Industry-University Cooperation, Asan-si (KR)

(*) Notice: Subject to any disclaimer, the term of this patent is extended or adjusted under 35 U.S.C. 154(b) by 0 days.

(21) Appl. No.: 14/527,080

(22) Filed: Oct. 29, 2014

(65) Prior Publication Data

US 2016/0123891 A1 May 5, 2016

(51) Int. Cl.
*G01B 11/24* (2006.01)
*G01N 21/88* (2006.01)
*G01B 11/25* (2006.01)
*G01N 21/95* (2006.01)

(52) U.S. Cl.
CPC ........... *G01N 21/8806* (2013.01); *G01B 11/24* (2013.01); *G01B 11/25* (2013.01); *G01N 21/9501* (2013.01); *G01N 2201/061* (2013.01)

(58) Field of Classification Search
CPC ... G01B 11/25; G01B 11/2518; G01B 11/24; G01N 21/9501
See application file for complete search history.

(56) References Cited

U.S. PATENT DOCUMENTS

| | | | | |
|---|---|---|---|---|
| 2002/0167662 A1* | 11/2002 | Tanaami | ............ | G01N 21/6428 356/318 |
| 2010/0118123 A1* | 5/2010 | Freedman | ............... | G01B 11/25 348/46 |
| 2014/0139630 A1* | 5/2014 | Kowalevicz | ........... | G03B 17/00 348/46 |
| 2015/0028188 A1* | 1/2015 | Kowalevicz | ...... | H01L 27/14625 250/208.1 |
| 2015/0165551 A1* | 6/2015 | Holmgren | .......... | B23K 26/0648 219/121.75 |
| 2016/0124295 A1* | 5/2016 | Montgomery | ....... | G03B 21/625 353/10 |

* cited by examiner

*Primary Examiner* — Kara E Geisel
*Assistant Examiner* — Shawn Decenzo
(74) *Attorney, Agent, or Firm* — NSIP Law

(57) ABSTRACT

The present invention relates to an inspection apparatus, the inspection apparatus including a projection unit configured to project a plurality of lights, each having a different focal length relative to a surface of an inspection object, and an inspection unit configured to inspect a surface of an inspection object using the light reflected from the inspection object, wherein the projection unit is provided with a plurality of lenses configured to project the lights, and curvature of each lens is different, and the focal length is different due to the difference of the curvature, whereby the curve on a surface of the inspection object can be reliably measured.

4 Claims, 5 Drawing Sheets

APPARATUS FOR INSPECTING

FIELD

The present invention relates to an apparatus for inspecting configured to inspect a curve on a surface of samples as inspection objects.

BACKGROUND

When curves or bends existing on the surfaces of samples such as semiconductor wafers, electronic substrates and steel plates have any effects on the properties of products, there is a need to measure the curves or the bends of relevant products.

For example, when laser beam is projected on a sample as an inspection object, using a laser distance measurement sensor, and a distance between the measurement sensor and the object is measured by receiving a laser beam reflected from the object, and if the measured distance is constant, it may be determined that the object is flat.

However, when the laser distance measurement sensor is used, there is a disadvantage in that it is very expensive to install the laser distance measurement sensor, and a control is required to move the laser distance measurement sensor for application to a broader scope.

Another disadvantage is that inspection time is lengthened, because a small number of laser distance measurement sensors are used to inspect an object. As a conventional apparatus for inspecting a surface of an object, Korea Registered Patent Publication No.: 0564323 is disclosed with a technique to measure a bend generated on an object, using a laser distance measurement sensor. However, the Korea Registered Patent Publication No.: 0564323 is still fraught with the limitations possessed by the laser distance measurement sensor.

PRIOR ART

Patent Document (Patent Document 1): Korea Registered Patent Publication No.: 0564323

DISCLOSURE

Subjects

The present invention is to provide an apparatus for inspecting (hereinafter referred to as 'inspection apparatus') configured to reliably measure curves existing on a surface of an object and to measure the curves at a high speed.

It should be emphasized, however, that the present disclosure is not limited to a particular disclosure, as explained above. It should be understood that other technical subjects not mentioned herein may be appreciated by those skilled in the art.

Solution

In one general aspect of the present invention, there is provided an inspection apparatus, the inspection apparatus comprising:

a projection unit configured to project a plurality of lights, each having a different focal length relative to a surface of an inspection object; and an inspection unit configured to inspect a surface of an inspection object using the light reflected from the inspection object, wherein the projection unit may be provided with a plurality of lenses configured to project the lights, and curvature of each lens may be different, and the focal length may be differentiated by the difference of the curvature.

Preferably, but not necessarily, each lens may be arranged on an xy plane when the inspection object moves to an x axial direction on the xy plane, the curvature of each lens may be different according to an x axial direction on the arrangement of each lens, and the focal length may be differentiated by difference of curvature.

Furthermore, the inspection unit may grasp a focal length of a focus as a distance from the inspection object, when a focus of the light projected from the projection unit matches a surface of the inspection object, and may determine the curve of the surface of the inspection object using the grasped distance.

Preferably, but not necessarily, the projection unit includes a light source configured to generate a light, and an MLA (Micro Lens Array) of first region formed with a plurality of lenses configured to generate a focus of the light, wherein the projection unit includes an extension unit configured to expand the light outputted from the MLA to a second region greater than the first region on a plane, and wherein the extension lens unit may include a telecentric lens.

In another general aspect of the present invention, there is provided an inspection apparatus, the inspection apparatus comprising:

a light source unit configured to generate lights of same wavelength;

a first lens unit configured to convert an optical path of light radially projected from the light source to a straight line; and a second lens unit provided with a plurality of lenses configured to form a focus of the light outputted from the first lens unit and to relatively move to an x axis relative to an inspection object arranged on a first xy plane, wherein a curvature of each lens of the second lens unit may be different and a focal length may be differentiated by the difference of the curvature.

Preferably, but not necessarily, the second lens may be arranged a second xy plane having a different z value from that of the first xy plane in a xyz space, and may include a path conversion unit configured to convert a path of light outputted from the first lens to a direction perpendicular to the second xy plane and project the path of light to the second lens unit, wherein the inspection apparatus may further include an inspection unit configured to grasp a distance between the second lens and a surface of the inspection object, and the path conversion unit may project a reflective light to the inspection unit by receiving the reflective light.

Preferably, but not necessarily, the inspection apparatus further comprises a third lens unit arranged between the second lens unit and the inspection object to increase a distance of each focus formed by the second lens unit on the xy plane.

In still another general aspect of the present invention, there is provided an inspection apparatus, the inspection apparatus comprising a lens unit where light incident to a first surface is outputted to a second surface, and at least one of the first and second surfaces may be formed with a plurality of lenses each having a different curvature.

Advantageous Effect

The inspection apparatus according to the present invention has an advantageous effect in that a plurality of focuses each having a different focus length can be formed using a plurality of lenses each having a different curvature, and a curve on a surface of an inspection object can be reliably measured at a high speed, using each focal length.

DETAILED DESCRIPTION

Figure 1:
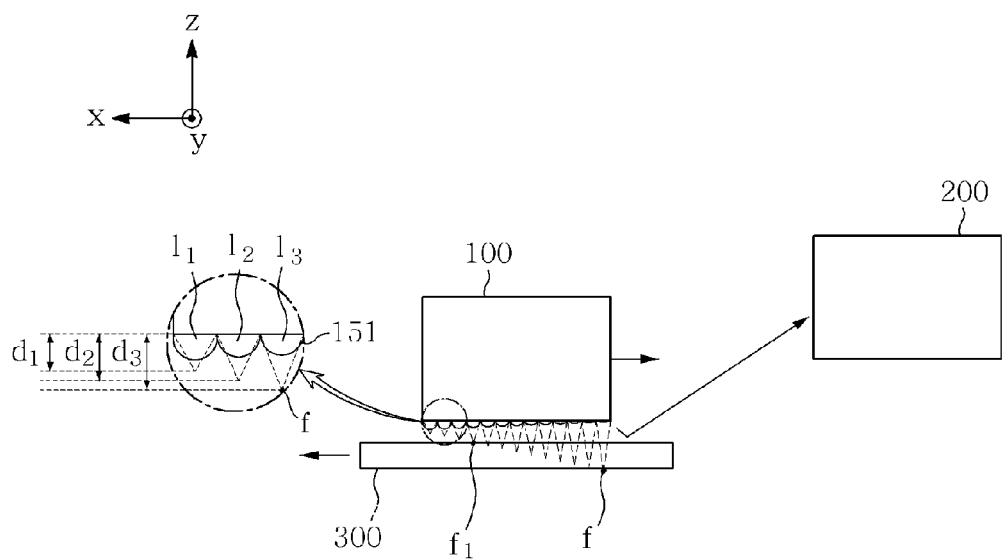
FIG. 1 is a schematic view illustrating an inspection apparatus according to the present invention.

Hereinafter, exemplary embodiments of the present disclosure will be described in detail with reference to the accompanying drawings. In the drawings, the size and relative sizes of layers, regions and/or other elements may be exaggerated or reduced for clarity and convenience.

Accordingly, the meaning of specific terms or words used in the specification and claims should not be limited to the literal or commonly employed sense, but should be construed or may be different in accordance with the intention of a user or an operator and customary usages. Therefore, the definition of the specific terms or words should be based on the contents across the specification.

FIG. 1 is a schematic view illustrating an inspection apparatus according to the present invention.

The inspection apparatus according to the present invention illustrated in FIG. 1 may include a projection unit (100) and an inspection unit (200).

The projection unit (100) may project a plurality of lights each having a different focal length relative to a surface of an inspection object (300).

The inspection object (300) is an object on which the plurality of lights outputted from the projection unit (100) is projected, and an object that may have an effect on physical properties of surfaces of objects such as semiconductor wafers, electronic substrates and steel plates.

The inspection apparatus according to the present invention uses lights in order to inspect curves or bends existing on the surfaces of the inspection object (300). At this time, the lights may be lights having various wavelengths or having a single wavelength. It may be advantageous to use a light of single wavelength for formation of a reliable focus.

The projection unit (100) may form a focus to a direction facing the inspection object (300) using a lens instead of simply projecting a light on a surface of the inspection object. At this time, a plurality of focuses may be formed where each focus length of the focuses may be mutually different. The projection unit (100) may use a curvature of a lens (151) in order to project a plurality of lights, each having a different focal length.

The focus is a point that determines an optical property of the lens (151). The light parallel incident on an optical axis passes a point which is ½ of a radius of curvature, where the point is a focus. A focal length is a distance between a focus and a main point of the lens (151), where the focal length increases as the focus is formed at an area distant from the lens (151).

Furthermore, the focus is distantly formed as the radius of curvature increases. The curvature is reversely proportionate to the radius of curvature, where as the curvature increases, the focus is formed near to the lens (151), and as the curvature decreases, the focus is distantly formed from the lens (151).

In other words, as the curvature decreases, the focal length increase, and as the curvature increases, the focal length decreases. For example, as illustrated in FIG. 1, when configuration is made in such a manner that focal lengths are increased as d1, d2, d3 toward negative direction of x axis, a plurality of lenses (151) is arranged to an x axis direction, and curvatures of each lens (151), e.g., a lens 11, a lens 12, and a lens 13 are made to decrease toward negative direction of x axis.

When the inspection object (300) moves to x axis direction on an xy plane, the projection unit (100) may include a plurality of lenses (151) arranged on the xy plane. In order to prevent the inspection object (300) from colliding with the projection unit (100), z axis coordinate of the inspection object (300) and projection unit (100) may be different on an xyz space. In this case, curvature of each lens (151) may be mutually different in arrangement of each lens (151) along the x axis direction, and the focal length may be also changed due to the difference of curvature of each lens (151).

According to this configuration, the light projected from the projection unit (100) may form a focal length that is lengthened to z axis when facing to one direction along x axis as illustrated in FIG. 1. In other words, a plurality of focuses formed by the projection unit (100) may have mutually different coordinates on the z axis. When the inspection object (300) is exposed to an environment formed with the plurality of focuses through the projection unit (100), curves on the surface of the inspection object (300) can be inspected. This inspection may be performed by the inspection unit (200).

The inspection unit (200) can inspect a surface of the inspection object (300) using the light reflected from the inspection object (300). When the light projected from the project unit (100) is reflected from the inspection object (300), and when the reflected light is projected to a predetermined position, a specific shape appears. Analysis of the specific shape can check whether the projected light is in focus. If it is determined that the projected light is in focus, a relevant focus length may be determined as a distance between the projection unit (100) and the inspection object (300).

The projection unit (100) is formed with a plurality of focuses each having a different focus length to a z axis direction, such that any one focus fl of the focuses is formed on a surface of the inspection object (300). Of course, there is a need of setting, by the inspection object (300), a focus length within an estimated scope of curves.

In other words, the inspection unit (200) may grasp a focus length of a relevant focus as a distance from the inspection object (300), when the surface of the focus f1 of light projected from the projection unit (100) matches the surface of the inspection object (300). Furthermore, the curve on the surface of the inspection object (300) can be determined by the grasped distance.

For example, when the distance grasped by the inspection unit (200) is constant across the inspection object, it can be viewed that there is no curve on the surface of the inspection object (300), and when the grasped distance is not constant, it can be viewed that there is a curve on the surface of the inspection object (300). Furthermore, an abnormal position can be grasped by checking, by the inspection object (300), a portion (coordinate) where the distances are different.

Thus, in order to allow the inspection unit (200) to reliably perform the inspection, there is a need to know a portion of the inspection object (300) captured by a relevant focus. It is assumed in the present specification that the portion of the inspection object (300) where the focus is formed is grasped by a separate means.

Figure 2:
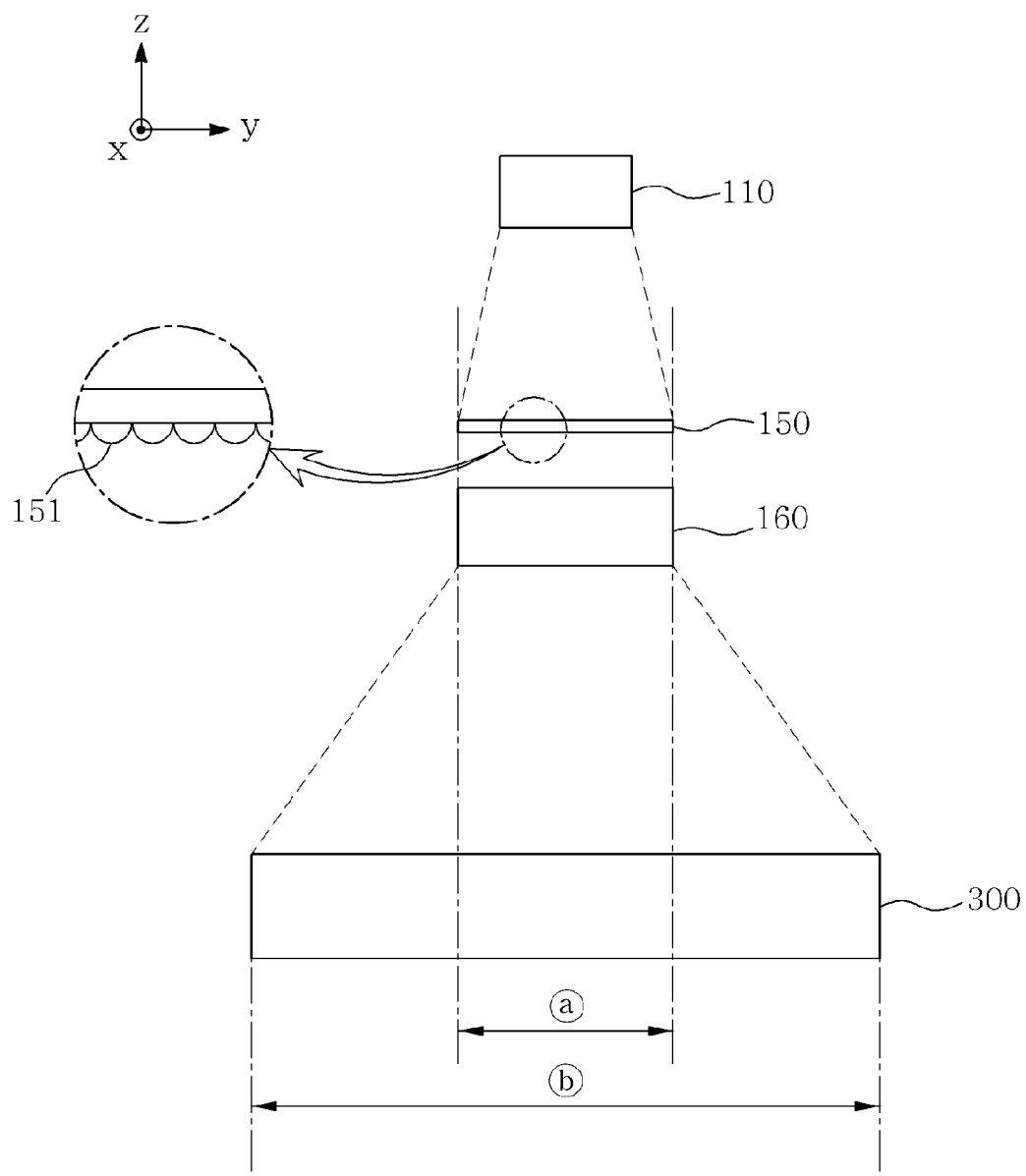
FIG. 2 is a schematic view illustrating a projection unit forming an inspection apparatus according to the present invention.
Figure 3:
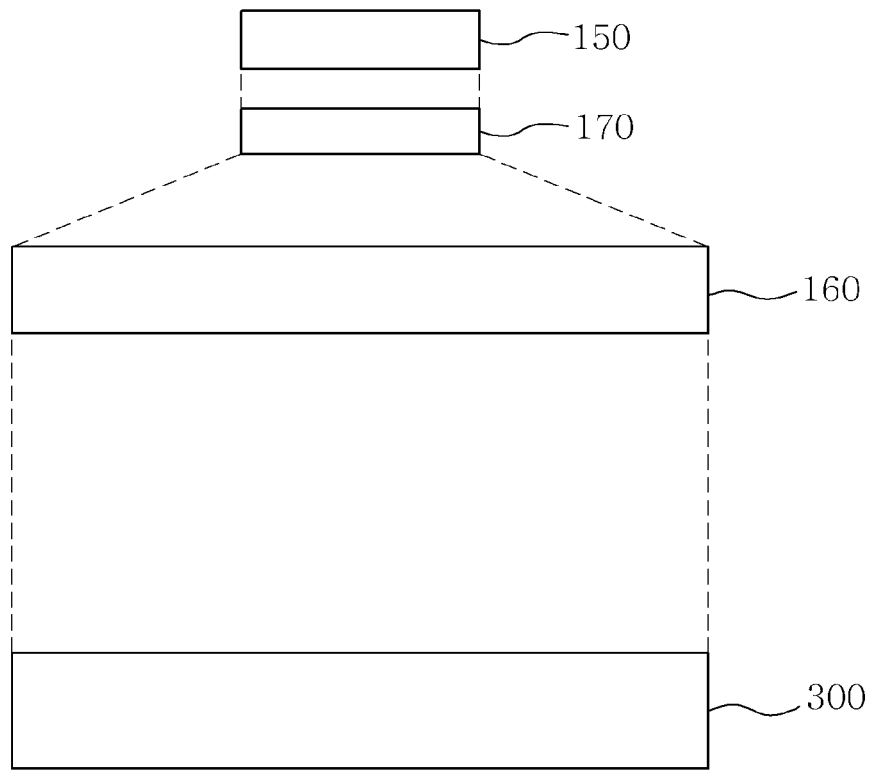
FIG. 3 is a schematic view illustrating another projection unit forming an inspection unit according to the present invention.

FIG. 2 is a schematic view illustrating a projection unit (100) forming an inspection apparatus according to the present invention, and FIG. 3 is a schematic view illustrating another projection unit (100) forming an inspection unit according to the present invention.

The projection unit (100) may include a light source (110) configured to generate lights, and an MLA (Micro Lens Array, 150) of first region formed with a plurality of lenses (151) configured to generate focuses of lights by receiving the lights generated by the light source (110).

The MLA (150) is a member formed by the plurality of lenses (151), and when a light is incident on an input side, a plurality of focuses may be formed through the lens (151) at an output side. When an area formed by the MLA (150), or areas of lenses (151) forming the MLA (150) is defined as a first region, an extension lens (160) may be used to expand a size of the first region.

When the inspection object (300) moves to an x axis direction in FIG. 1, and when the length of the inspection object (300) is longer to a y axis direction (width of first region) in the first region than (or exceeds) the length of y axis direction (width of inspection object 300), the projection unit (100) may not move to scan the inspection object (300) to the y axis direction. However, the width of the first region may be smaller than the width of the inspection object (300) depending on the size of the inspection object (300).

The extension lens (160) may expand, on a plane, a light outputted from the MLA (150) to a second region lager than the first region of the MLA (150). The width of the second region may be more than the width of the inspection object(300).

The width ⓐ of the first region in FIG. 2 is smaller than the width ⓑ of the first region. In order to inspect the inspection object (300) using the width ⓐ of the first region, the inspection object (300) and the projection unit (100) must relatively move to the x axis, and also must relative move to the y axis. However, when the extension lens (160) is arranged between the MLA (150) and the inspection object (300), the size of the first region, particularly the width ⓐ can be expanded over the width ⓑ of the inspection object (300). FIG. 2 illustrates that the width of the second region is same as the width of the inspection object (300).

The extension lens (160) may be formed with various lenses. For example, the extension lens (160) may include a telecentric lens. When the extension lens is formed with the telecentric lens, an optical axis from the inspection object (300) to the extension lens (160) can be straight, and may inspect an object regardless of perspective values, stairs or angles.

The telecentric lens may be formed in a size of the second region, whereby the extension lens (160) may include an auxiliary lens (170) configured to expand an output light outputted in a size of the first region between the MLA (150) and the telecentric lens to match an input terminal of the telecentric lens.

Referring to FIG. 2, all the curvatures of the lenses (151) formed on the MLA are indicated in the same size, where the curvatures of the lenses (151) may be same when the inspection object and the MLA relatively move to the x axis direction, as long as the curvature of the lens (151) is different only to the x axis direction.

In other words, the curvatures of the lenses (151) arranged on (x, y) position on the same x axis coordinate may be mutually same. For example, when lenses are on x1~x5 coordinates on the x axis and y1~y17 coordinates on the y axis, the curvatures of lenses (151) arranged on the (x1, y1)~(x1, y17) coordinates may be same.

Figure 4:
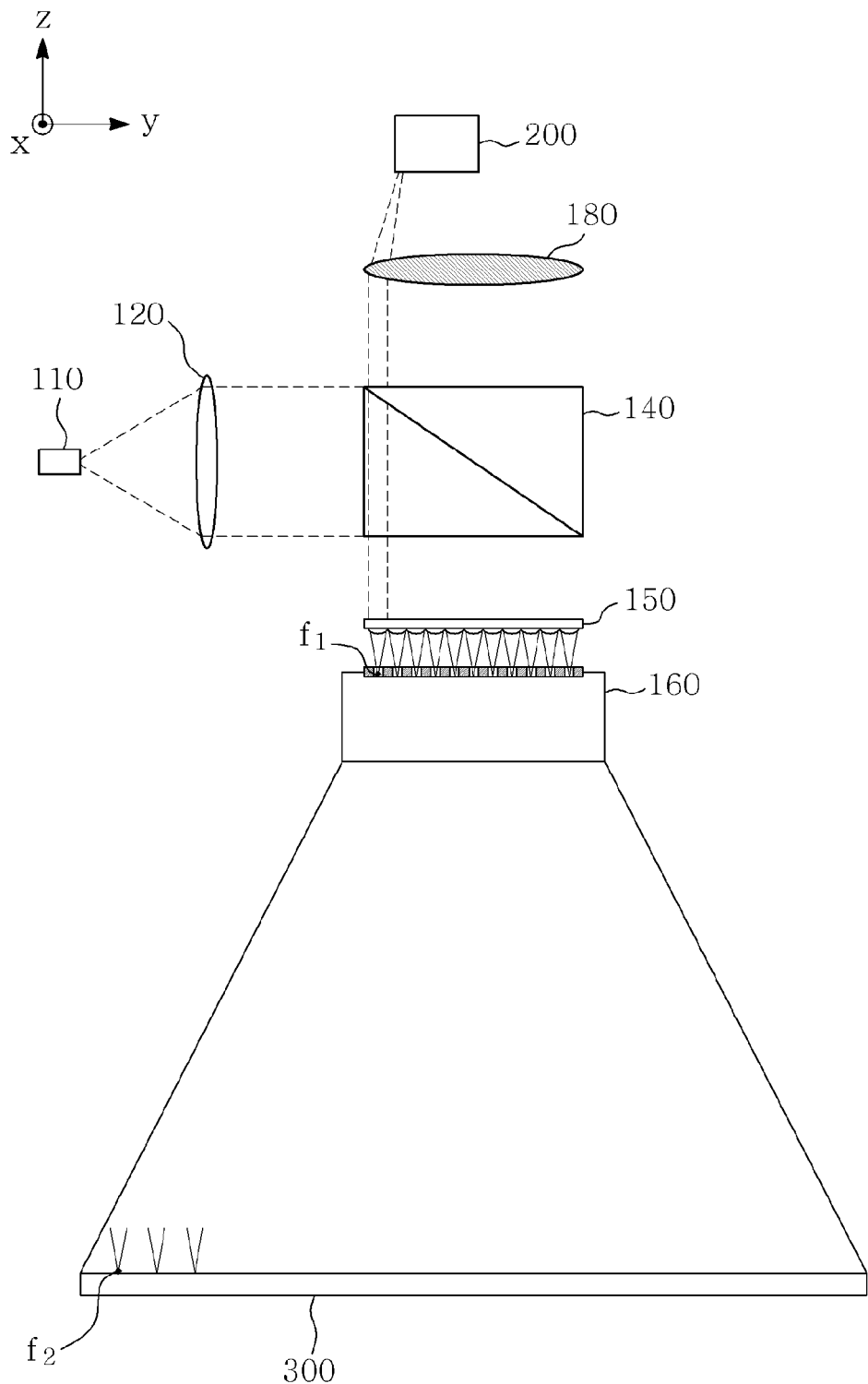
FIG. 4 is a schematic view illustrating another inspection apparatus according to the present invention.

FIG. 4 is a schematic view illustrating another inspection apparatus according to the present invention.

The inspection apparatus according to the present invention may include a light source (110), a first lens unit (120) and a second lens unit. The light source (110) may generate lights of same wavelength.

The first lens unit (120) may change an optical path of light radially projected from the light source (110) to a straight line. The lights generated from the light source (110) may be diffused to all directions according to the physical properties of lights and may have a radial projection angle. The light radiated from the light source (110) by the first lens unit (120) is propagated to a straight path to allow a path conversion unit (140) or the second lens unit to use the light easily.

The second lens unit may be provided with a plurality of lenses (151) configured to form a focus of light outputted from the first lens unit. For example, the second lens unit may include the MLA (150) as discussed in the foregoing. The second lens unit may relatively move to the x axis direction relative to an inspection object arranged on a first xy plane. The curvatures of each lens (151) forming the second lens unit may be different each other, and a distance of focus may be changed due to differences of curvatures.

An area formed by the focuses outputted from the second lens unit is the first region as discussed in the foregoing, where the first region may be same as the area of light outputted from the path conversion unit (140).

The second lens unit may be arranged on a second xy plane having a z value different from that of the first xy plane in the xyz space. The light outputted from the first lens unit must be incident on a direction perpendicular to the second xy plane arranged with the second lens unit, where it may be difficult to arrange the first lens unit to an appropriate position thereto. As a measure to cope with the difficulty, the inspection apparatus may include a path conversion unit configured to project to the second lens unit the path of light outputted from the first lens unit to a direction perpendicular to the second xy plane.

A third lens unit may be arranged between the second lens unit and the inspection object (300). The third lens unit may increase a distance of each focus formed by the second lens unit on the xy plane. The third lens unit may include the extension lens (160) as discussed in the foregoing.

Figure 5:
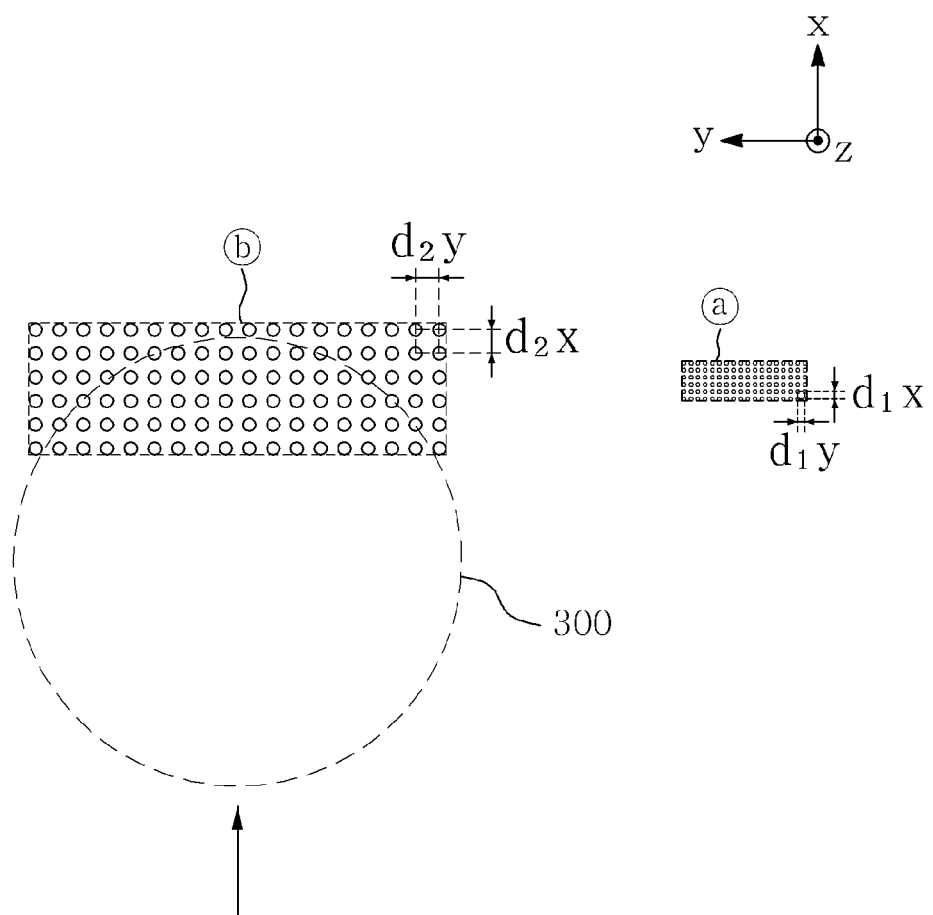
FIG. 5 is a schematic view illustrating an area of light projected to an inspection object by an inspection apparatus according to the present invention.

FIG. 5 is a schematic view illustrating an area of light projected to an inspection object (300) by an inspection apparatus according to the present invention.

Referring to FIG. 5, it can be noted that distances d2x, d2y of focuses included in the second region are greater than distances d1x, d1y included in the first region ⓐ, whereby a coordinate of the focus f1 formed by the second lens unit may differ from a coordinate of focus f2 formed in response thereto by the third lens unit. Furthermore, an area of the second region grows larger than an area of the first region.

The size of the second region at this time may be determined by the width of the inspection object (300). Although resolution deteriorates as the distances of each focus is increased by the third lens unit, there may be generated no particular problems as long as more focuses are formed. Of course, it should be apparent that the number of lenses (151) forming the second lens unit must be appropriately increased in response thereto.

Referring to FIG. 4 again, the inspection apparatus according to the present invention may include an inspection unit (200).

The inspection unit (200) may grasp a distance from the path conversion unit (140) or from the surface of the second lens unit and the inspection object (300) by receiving a light reflected from the inspection object (300). The inspection unit (200) can grasp the curve on the surface using the distance thus grasped.

Meantime, the path conversion unit (140) may project a light reflected from the inspection object (300) to the inspection unit (200) by receiving the light. In this case, the path conversion unit (140) may be an optical means configured to output the light inputted from the first direction (e.g., light source side) to the second direction, and to output the light inputted from the second direction (e.g., inspection object) to a third direction.

A projection lens (180) configured to project a light outputted from the path conversion unit (140) to the inspection unit (200) may be interposed between the path conversion unit (140) and the inspection unit (200).

The inspection apparatus according to the present invention thus described can inspect the curves of the inspection object (300) by forming a focus having mutually different coordinates to the z direction by using a curvature of the lens (151), and moving the inspection object (300) within a focus scope to the z axis direction, and by grasping a focus length of focus matching to the surface of the inspection object (300).

To wrap up, the inspection apparatus according to the present invention as the MLA (150) may include a lens unit on which a light incident on the first surface can be outputted to the second surface.

At this time, a plurality of lenses (151) each having a different curvature may be formed on at least one of the first surface and the second surface. As a result, a plurality of focuses each having a different focus length can be generated, and the curves and bends of the inspection object (300) can be inspected using the focus.

The configuration thus described can, reliably and at a high speed, inspect the inspection object (300) at a reasonable price and then some.

The above-mentioned inspection apparatus according to the present invention may, however, be embodied in many different forms and should not be construed as limited to the embodiments set forth herein. Thus, it is intended that embodiments of the present invention may cover the modifications and variations of this invention provided they come within the scope of the appended claims and their equivalents. While particular features or aspects may have been disclosed with respect to several embodiments, such features or aspects may be selectively combined with one or more other features and/or aspects of other embodiments as may be desired.

The invention claimed is:

1. An inspection apparatus, the inspection apparatus comprising:
a projector configured to project a plurality of lights, each having a different focal length relative to a surface of an inspection object; and
an inspector configured to inspect a surface of the inspection object using the light reflected from the inspection object, wherein the projector is provided with a plurality of lenses configured to project the lights, and curvature of each lens is different, and the focal length is different due to the difference of the curvature,
wherein each lens is arranged on an xy plane, and the inspection object moves to an x axial direction on the xy plane, the curvature of each lens is different according to an x axial direction on the arrangement of each lens, and the focal length is differentiated by difference of curvature,
wherein the projector includes a light source configured to generate a light, and a MLA (Micro Lens Array) of a first region formed with a plurality of lenses configured to generate a focus of the light, wherein the projector includes an extension lens configured to expand the light output from the MLA to a second region having a greater area than the first region on a plane,
wherein the extension lens comprises a telecentric lens,
wherein an optical axis from the inspection object to the extension lens is straight, and the inspection object is inspected substantially regardless of perspective values, stairs, or angles of the inspection object.

2. An inspection apparatus, the inspection apparatus comprising:
a light source configured to generate lights of a substantially same wavelength;
a first lens configured to change a path of light radially projected from the light source to a straight line;
a second lens provided with a plurality of lenses configured to form a focus of the light output from the first lens and to be relatively moved to an x axis direction relative to an inspection object arranged on a first xy plane, wherein a curvature of each lens of the second lens is different, and a focal length is differentiated by the difference of the curvature; and,
a third lens including a telecentric lens configured to receive the light and impinge the light on the inspection object.

3. The inspection of claim 2, wherein the third lens is arranged between the second lens and the inspection object to increase, on the xy plane, a distance of each focus formed at the second lens.

4. An inspection apparatus, the inspection apparatus comprising:
a micro lens array (MLA) configured to transmit a light incident on a first surface thereof to a second surface thereof, wherein a plurality of lenses, each having a different curvature, is formed on at least one of the first surface and the second surface; and,
an extention lens receiving the light from the second surface of the MLA and configured to transmit the light to impinge on an inspection object, wherein the extension lens includes a telecentric lens.

* * * * *